United States Patent [19]

Curran et al.

[11] Patent Number: 5,744,605
[45] Date of Patent: Apr. 28, 1998

[54] INTERMEDIATES IN THE SYNTHESIS OF (+) CAMPTOTHECIN AND RELATED COMPOUNDS AND SYNTHESIS THEREOF

[75] Inventors: Dennis P. Curran; Hui Liu, both of Pittsburgh, Pa.; Maree Patricia Collis, Prahran, Australia

[73] Assignee: University of Pittsburgh, Pittsburgh, Pa.

[21] Appl. No.: 609,900

[22] Filed: Mar. 4, 1996

Related U.S. Application Data

[63] Continuation of Ser. No. 85,190, Jun. 30, 1993, abandoned.
[51] Int. Cl.[6] .................. C07D 487/04; C07D 471/14; C07D 213/64; C07B 37/10
[52] U.S. Cl. .................. 546/70; 544/343; 546/302
[58] Field of Search .................. 544/343; 546/70

[56] References Cited

PUBLICATIONS

Curran et al JACS 114, 5863 (1992).
Potmesil Cancer Research 54, 1431-9 (1994).
Slichenmyer, JNCI 85, 271 (1993).
Creemers, Cancer Treatment Rev 20, 73-96 (1994).
Sugimori, Heterocydes 38, 81 (1994).
Gottlieb, Cancer Chemotheraps Reports Part 1 vol. 56, p. 103 (1972).
Moertel, Cancer Thoms. Reporst Part 1 vol. 56, p. 95 (1972).

*Primary Examiner*—Mark L. Berch
*Attorney, Agent, or Firm*—Bartony Hare & Edson

[57] ABSTRACT

The present method provides a short, convergent total synthesis of novel intermediates in the synthesis of (±)-camptothecin and related compounds. The synthesis scheme includes a novel 4+1 radical annulation followed by another cyclization to simultaneously assemble rings B and C of the Camptothecin compound. In the synthesis, the following novel precursor is reacted with a phenyl isocyanide:

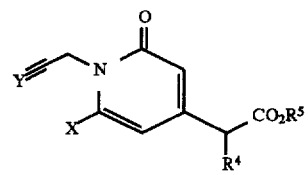

The resulting tetracyclic intermediates comprise a quinoline fused to a pyrrolidine ring, with the pyrrolidine ring being fused to an alpha-pyridone ring. The tetracyclic intermediates thus comprise the A, B, C, and D rings characteristic of camptothecin and camptothecin derivatives, and are easily convertible to camptothecin and camptothecin derivatives via hydroxymethylation and oxidation.

6 Claims, 11 Drawing Sheets

12a

12b

12c

12d

INTERMEDIATES IN THE SYNTHESIS OF (+) CAMPTOTHECIN AND RELATED COMPOUNDS AND SYNTHESIS THEREOF

This application is a continuation of application Ser. No. 08/085,190, filed on Jun. 30, 1993, abandoned the contents of which are hereby incorporated by reference.

FIELD OF THE INVENTION

The present invention relates to novel intermediates in the synthesis of (±)-camptothecin and related compounds, and to a synthesis of camptothecin and related compounds via a 4+1 radical annulation.

BACKGROUND OF THE INVENTION

As part of an antitumor screening program, Wall and coworkers identified the novel pyrrolo [3,4-b] quinoline alkaloid (S)-camptothecin in 1966. Wall, M. E., et al., *J. Am. Chem. Soc.*, 88, 3888 (1966); Carte, B. K., et al., *Tetrahedron*, 46, 2747 (1990). The chemical formula of (S)-camptothecin is provided below.

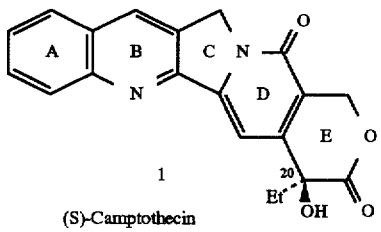

(S)-Camptothecin

This compound had been isolated from the extracts of the *camptotheca acuminata* tree. In addition to its novel structure, camptothecin has two other unusual features: its quinoline nitrogen is not very basic, and its α-hydroxy lactone is quite reactive. For a few years, camptothecin appeared to be an exciting lead compound for cancer chemotherapy. However, initial medical excitement waned because of the relative insolubility of camptothecin. Moreover, clinical trials of a water-soluble sodium salt derived by opening the lactone of camptothecin were abandoned because of unpredictable toxicity problems. The sodium salt is considerably less potent than camptothecin and its activity is now thought to result from lactonization to reform camptothecin in vivo.

Camptothecin was synthesized about ten times during the 1970s, although some later syntheses are modifications of earlier ones. Syntheses based on the Friedlander quinoline synthesis to construct ring B were most common. Ejima, A., et al., *J. Chem. Soc., Perkin Trans.* 1, 27 (1990); Earl, R. E. and Vollhardt, K. P. C., *J. Org. Chem.* 1984, 49, 4786; Ihara, M. et al., *J. Org. Chem.*, 48, 3150 (1983); Cai, J. C. and Hutchinson, C. R., *Chem. Heterocycl. Compd.* 25, 753 (1983); Hutchinson, C. R., *Tetrahedron* 37, 1047 (1981); Cai, J. C. and Hutchinson, C. R., *The Alkaloids: Chemistry and Pharmacology;* Brossi, A. Ed.; Academic Press: New York, Vol. 21, p. 101 (1983); Schultz, A. G., *Chem. Rev.* 73, 385 (1973). Many syntheses are racemic, but resolutions have been reported. See Wani, M. C., et al. *J. Med. Chem.*, 30, 2317 (1987). More recently, a chiral auxiliary approach to asymmetric ethylation was described. See Ejima, A., et al., *Tetrahedron Lett.*, 30, 2639 (1989). Following the medicinal lead, synthetic interest in camptothecin peaked in the late 70s, and then began to wane.

Oncological and medicinal interest in camptothecin was reborn in the mid 80s when details about camptothecin's unique mechanism of action began to unfold. Camptothecin acts on DNA through the intermediacy of the enzyme topoisomerase I. Hsiang, Y. H., et al., *J. Biol. Chem.* 260, 14873 (1985); Hsiang, Y. H. and Liu, L. F., *Cancer Res.*, 48, 1722 (1988); Liu, L. F., *Annu. Rev. Biochem.*, 58, 351 (1989); "Chemotherapy: Topoisomerases as Targets," *Lancet*, 335, 82 (1990). The topoisomerases solve topological problems of DNA. Human topoisomerase I (100 kd) catalyzes the relaxation of supercoiled DNA by cleaving a single phosphodiester bond to form a temporary phosphoryl tyrosine diester. This intermediate is called the "cleavable complex." The other end of the cleaved strand is free, and can "unwind" before the DNA chain is resealed by reverse of the original reaction. Topoisomerase I acts without cofactors, its reactions are fully reversible, and it is thought to be especially important for unwinding DNA (thermodynamically favorable) during replication. In contrast, topoisomerase II acts by cleaving the resealing (after strand passage) both strands of DNA, and its reactions are coupled with ATP hydrolysis.

There is now very strong evidence that camptothecin kills cells by binding to and stabilizing the covalent DNA-topoisomerase I complex in which one strand of DNA is broken (the cleavable complex). The progression from the ternary camptothecin/topoisomerase I/DNA complex to cell death is not well understood, and is the subject of intense investigation. Several lines of evidence (including the complete reversibility of ternary complex formation) indicate that the ternary complex does not simply tie up DNA, but itself actively initiates cell death. For this reason, camptothecin is often called a "topoisomerase poison."

Until very recently, camptothecin and its close relatives were the only known topoisomerase I poisons. In contrast, there are now many known antitumor agents that are topoisomerase II poisons. These include large classes of intercalators like the acridines and anthracyclines that were originally thought to interact only with DNA. Such topoisomerase II poisons may be inherently less selective than camptothecin because their interactions with DNA do not require topoisomerase II. Important non-intercalative topoisomerase II poisons include members of the podophyllotoxin class.

Camptothecin is being touted as an unusually important lead in cancer chemotherapy because of its selectivity. The (potential) selective toxicity of camptothecin towards cancer cells emanates from two sources: 1) camptothecin is highly selective for the DNA/topoisomerase I cleavable complex, and 2) replicating cancer cells contain elevated levels of topoisomerase I (15-fold increases over normal cells have recently been measured).

Recent tests in xenografts by Potmesil and coworkers were very promising. See Giovanella, B. C., et al., *Science*, 246, 1046 (1989). Racemic 9-aminocamptothecin was found to be very effective in treating mice carrying colon cancer xenografts. Indeed most of the mice in the study were cured by 9-aminocamptothecin at dose levels that were well tolerated. The improved efficacy of 9-aminocamptothecin compared to current drugs used in colon cancer chemotherapy (like 5-fluorouracil) was dramatic. 10,11Methylenedioxycamptothecin also showed very good promise. Though it is still early, the significance of these results is very high. Human colon cancer is a major problem in clinical oncology, and one in twenty-five Americans will develop this disease during their lifetime.

Recent results are even more encouraging. See Giovanella, B. C., et al., *Cancer Res.*, 51, 3052 (1991). It has been discovered that (S)-camptothecin itself can be formulated in 20% interlipid, and that this formulation is active both intramuscularly and orally. These treatments were far superior to the intravenous ones. With this formulation, non-toxic doses of camptothecin suppressed growth and induced regression of cancer in thirteen human xenograft lines including colon, lung, breast, stomach, ovary, and malignant melanoma. Camptothecin was much less toxic than its sodium salt, and was more effective than any other clinical drug tested.

Other close relatives of camptothecin are also emerging as excellent candidates for chemotherapy against a variety of tumor types. Several such compounds are undergoing clinical trials. Curran, D. P., "The Camptothecins: A Reborn Family of Antitumor Agents," *J. of the Chinese Chem. Soc.*, 40, 1–6 (1993), the disclosure of which is incorporated herein by reference. See also Sawada, S., *Chem. Pharm. Bull.*, 39, 1446 (1991); Giovanella, B. C., et al., *Science* (Washington, D.C.), 246, 1046 (1989); Kingsbury, W. D., et al.; *Med. Chem.*, 34, 98 (1991); Sawada, S., et al.; *Chem. Pharm. Bull.*, 39, 1446(1991), Nicholas, A. W., et al. *J. Med. Chem.* 33, 972 (1991).

The excitement about camptothecin recently increased to even greater levels upon the discovery that it is a potent antiretroviral agent. Preil and coworkers showed that camptothecin and relatives: 1) inhibited retroviral topoisomerase I, 2) prevented retroviral infections in healthy cells, 3) reduced and eliminated retroviral infections and infected cells, and 4) did not harm cells at useful dose levels. Priel, E., et al., *AIDS Res. Hum. Retroviruses* 7, 65 (1991). Topoisomerase II inhibitors were ineffective. These results suggest that camptothecin may represents a new avenue of investigation for the potential treatment of AIDS.

Given the current interest in camptothecins, new directions in the total synthesis of this family of compounds would be welcome.

SUMMARY OF THE INVENTION

Accordingly, the present invention provides a short, convergent total synthesis of (±)-camptothecin and related compounds using a novel 4+1 radical annulation followed by another cyclization to simultaneously assemble rings B and C of camptothecin and related compounds.

Generally, the present invention provides a method of synthesizing tetracyclic compounds having the general formula

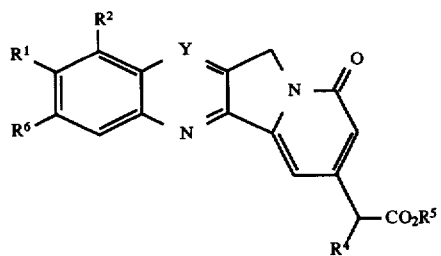

which are intermediates in many syntheses of (±)-camptothecin and related compounds. The conversion of these intermediates to (±)-camptothecin and related compounds is accomplished in two steps: hydroxymethylation and oxidation.

The synthesis of the tetracyclic intermediates comprises the step of a 4+1 radical annulation wherein the following novel precursor:

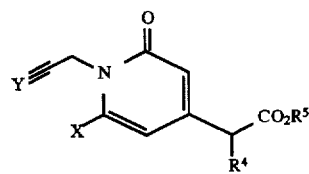

is reacted with an aryl isocyanide such as phenyl isocyanide. Y is preferably selected from the group consisting of —N and —CR$^3$. The aryl iscyanide may be unsubstituted, monosubstituted, disubstituted or trisubstituted.

R$^1$, R$^2$, R$^3$ and R$^6$ are preferably selected from the following groups: hydrogen, normal and branched alkyl groups, haloalkyl groups, perfluoroalkyl groups, allyl groups, benzyl groups, propargyl groups, alkoxyl groups, halo groups, substituted amino groups, substituted acylamino groups, cyano groups, acyl groups, substituted hydroxy alkyl groups, substituted amino alkyl groups. R$^4$ is preferably selected from primary or secondary alkyl, allyl, propargyl and benzyl groups. R$^5$ is preferably selected from linear or branched alkyl groups or benzyl groups. Most preferably, R$^5$ is selected from linear or branched alkyl groups in the range of C$_1$ to C$_6$.

The present synthetic route is useful for large-scale production of camptothecin and the production of new analogs of camptothecin for evaluation of biological activity.

DETAILED DESCRIPTION OF THE INVENTION

Model Reaction

Figure 1:
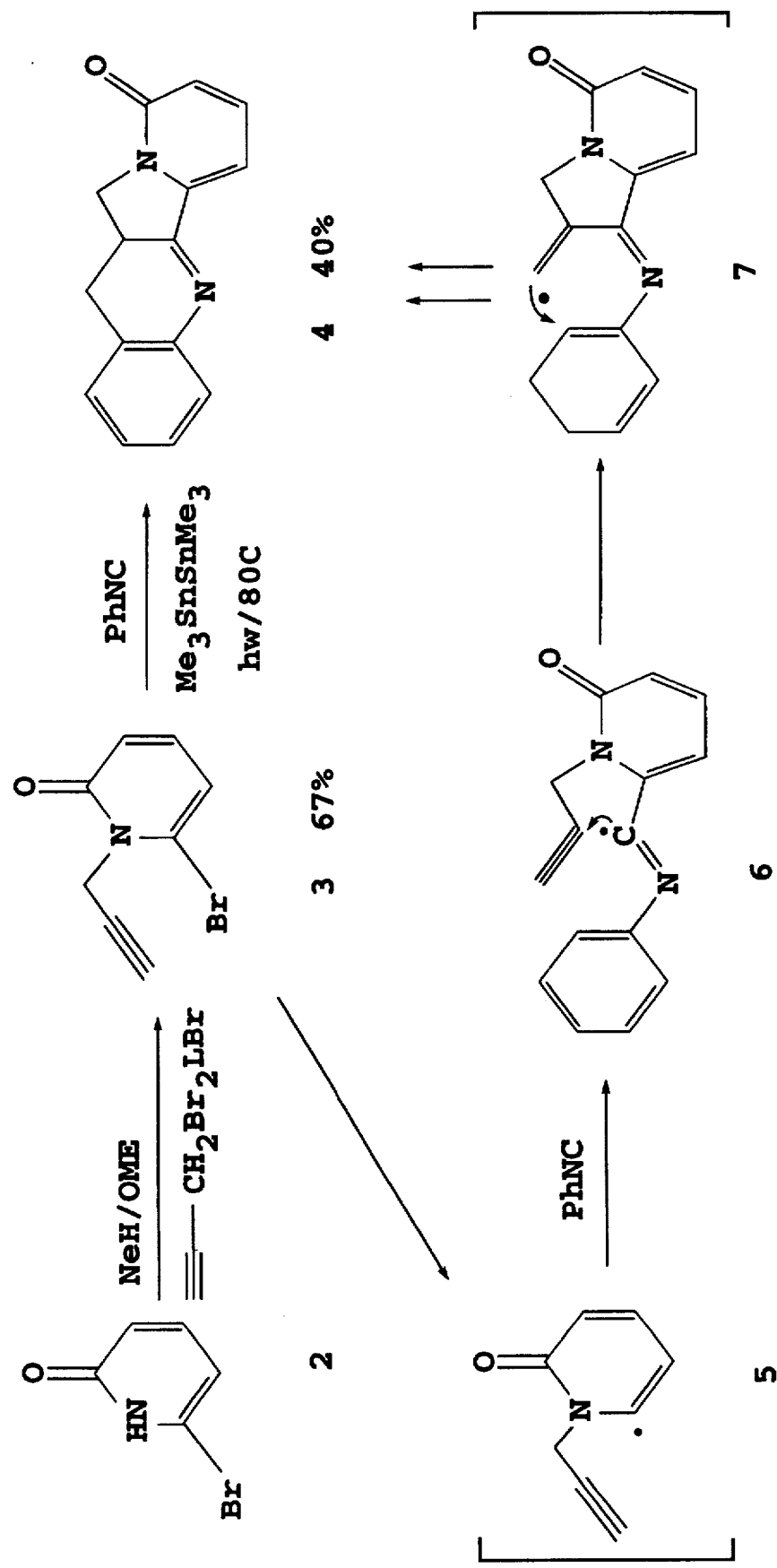
FIG. 1 is an illustration of the reaction scheme for a model 4+1 radical annulation.

The viability of the key 4+1 annulation was first demonstrated in the model reaction shown in FIG. 1.

In the reaction of FIG. 1, readily available bromopyridone 2 was N-propargylated to give 3. The synthesis of bromopyridone 2 is described in Newkome, G. R., et al, *Synthesis* 707 (1974), the disclosure of which is incorporated herein by reference. In turn, 3 reacted with phenyl isocyanide under conditions similar to those developed for reactions of simple pentynyl iodides. These conditions are detailed in Curran, D. P. and Liu, H., *J. Am. Chem. Soc.* 113, 2127 (1991), the disclosure of which is incorporated herein by reference.

Generally, an 80° C. benzene solution of 3 (1 equiv), phenyl isocyanide (PhNC) (5 equiv), and hexamethylditin (1.5 equiv) was irradiated with a sunlamp for 8 hr. After chromatography, the known tetracycle 4 was isolated in 40% yield as a white solid.

FIG. 1 also shows a hypothetical mechanism for the conversion of 3 to 4. Addition of pyridone radical 5 to phenyl isocyanide to give 6 is followed by two radical cyclizations and an oxidative rearomatization. Curran, D. P. and Liu, H., *J. Am. Chem. Soc.*, 113, 2127 (1991); Leardini, R. et al., *J. Org. Chem.*, 57, 1842 (1992); Bowman, W. R. et al., *Tetrahedron*, 47, 10119 (1991), the disclosures of which are incorporated herein by reference. See also Stork, G.; Sher, M. M., *J. Am. Chem. Soc.*, 105, 6765 (1983); Barton, D. H. R.; Ozbalik, N.; Vaher, B. *Tetrahedron*, 44, 3501 (1988).

Synthesis of (±)-Camptothecin

Figure 2:
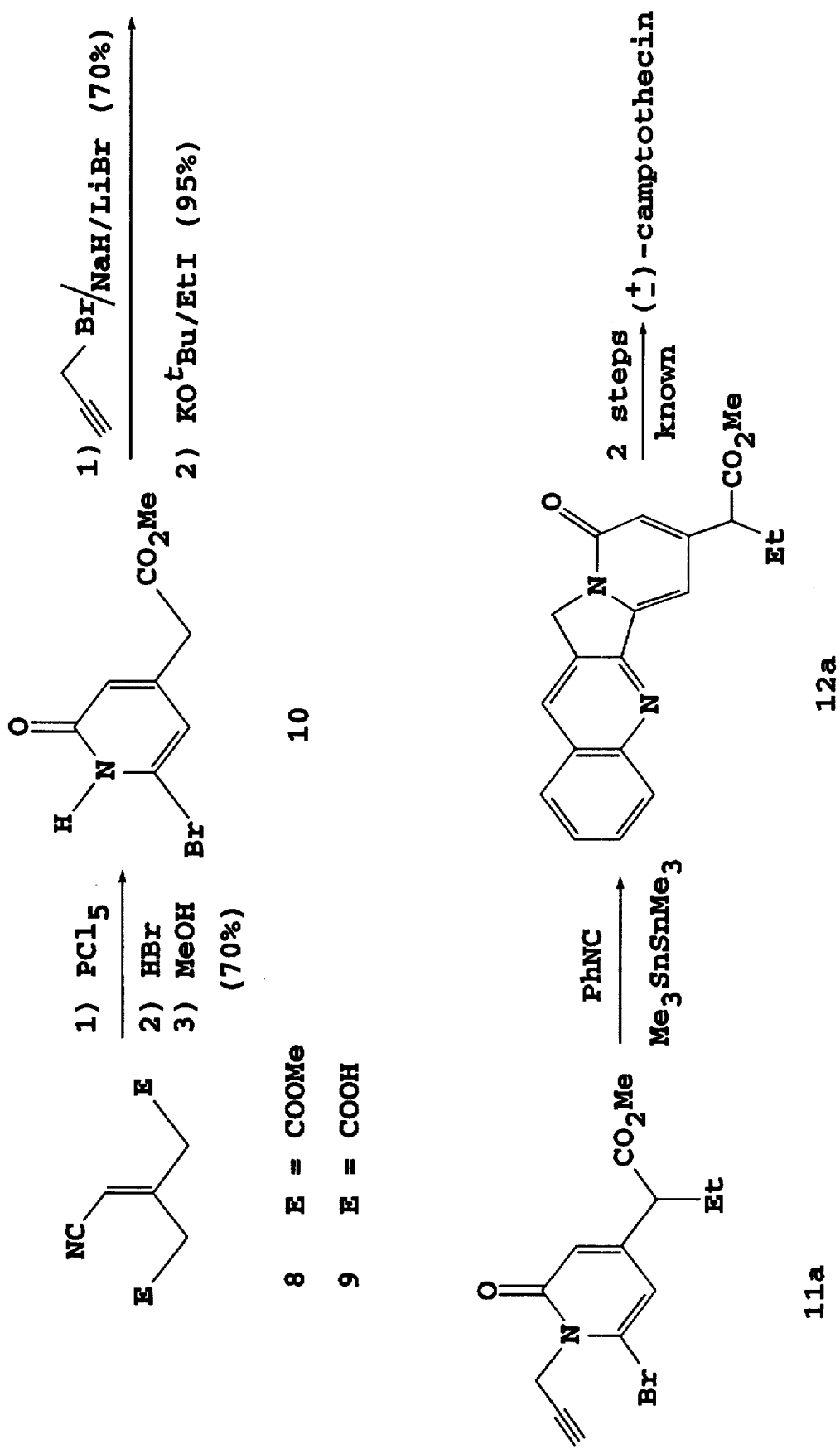
FIG. 2 is an illustration of a synthetic scheme for the synthesis of camptothecin via a 4+1 radical annulation.

The formal total synthesis of (±)-camptothecin is shown in FIG. 2. Nitrile 8 (dimethyl 3-(cyanomethylidene) pentanedioate) was first prepared by standard Doebner condensation of dimethyl acetonedicarboxylate and cyanoacetic acid (70%). See Simchen, G., *Chem. Ber.*, 103, 389 (1978). A flask equipped with a Dean-Stark water separator was charged with benzene (60 mL), dimethyl acetone-1,3-dicarboxylate (34.8 g, 0.2 mol), cyanoacetic acid (18.7 g, 0.22 mol), acetic acid (5.4 g, 0.09 mol), and ammonium acetate (3.1 g, 0.04 mol). The mixture was stirred for 5 minutes and then heated with an oil bath (oil temperature 130°–135° C.) until no more water was collected. Heating time was generally 6 hours and the water layer collected was around 6 mL. After the mixture was cooled to room temperature, cold water was added. This mixture was then extracted twice with ether. The combined organic phase was washed with water, saturated sodium bicarbonate solution, and brine, and dried over sodium sulfate. After removal of solvent, the crude product was purified by vacuum distillation to give 1.5 g of dimethyl acetone-1,3-dicarboxylate, and 27.2 g of nitrile 8 (104°–124° C./0.03 mm) as colorless liquid, yield 69–72%. Nitrile 8 was characterized as follows: $^1$H NMR (300 MHz, CDCl$_3$) δ 5.43 (1H, s), 3.57 (3H, s), 3.55 (3H, s), 3.45 (2H, s), 3.26 (2H, s); $^{13}$C NMR (75 MHz, CDC13) δ 168.8, 168.5, 151.7, 115.2, 102.6, 52.0 (2 C), 40.5, 38.8; IR (neat) 2224, 1738 cm$^{-1}$.

Standard saponification (KOH/EtOH) gave diacid 9. Conversion of diacid 9 to bromopyridone 10 (methyl 2-(6-bromo-2(1H)-pyridon-4-yl) acetate) was accomplished by modification of a known method to prepare chloropyridones. The diacid was first treated with PCl$_5$, and then gaseous HBr (10 equiv) was introduced. See Simchen, G., *Chem. Ber.*, 103, 389 (1978).

In general, potassium hydroxide (10 g, 180 mmol) was added to a 0° C. solution of nitrile 8 (7.88 g, 40 mmol) in ethanol (160 mL) with stirring. The reaction mixture was stirred at room temperature ("RT") for 2 days. After solvent removal, ice-water (100 mL) was added. Then the mixture was immersed in an ice-water bath, and 6N HCl was added slowly until the pH value reached to 1. This solution was saturated with sodium chloride, and extracted with ethyl acetate (70 mL×4). The combined organic phase was dried over sodium sulfate. After solvent removal under reduced pressure (via rotary evaporation and vacuum pumping), 6.87 g of 3-(cyanomethylidene) pentanedioic acid 9 was collected as yellow or orange solids.

These solids were crushed to powders and methylene chloride (270 mL) was added. The mixture was cooled to 0° C. and charged with phosphorus pentachloride (17.1 g, 82 mmol) under argon. The suspension was stirred at room temperature until all the white solids dissolved (3–9 h). The flask was cooled with an acetone-dry-ice bath, evacuated with an aspirator, and sealed.

Gaseous anhydrous hydrogen bromide (about 10 L, 400 mmol) was introduced and absorbed by the solution. The vacuum was then released by filling the vessel with argon. The flask was equipped with a drying-tube which was connected to a gas trap to absorb excess HBr. The solution was stirred at −78° C. for 1 h and at room temperature for 8 h. The reaction mixture was cooled to −78° C. again. Anhydrous methanol (15.4 g, 480 mmol) was added in one portion. The solution was then slowly warmed to room temperature and stirred for 2 more hours. After addition of ice-water (150 mL), two layers were separated. The aqueous layer was extracted with methylene chloride (100 mL×2). The combined organic phase was dried over sodium sulfate. After removal of solvent, the residue was applied to chromatography (silica gel, CHCl$_3$/EtOAC) to give 6.2 g of bromopyridone 10 as off-white solids, yield 63% (from nitrile 8). The product contained 3–8% of the 6-chloro analogue as detected by GC. $^1$H NMR (300 MHz, CDCl$_3$) δ 11.82 (1H, Br), 6.81 (1H, d, J=0.8 Hz), 6.60 (1H, d, J=0.8 Hz), 3.73 (3H, s), 3.53 (2H, s); $^{13}$C NMR (75 MHz, CDCl$_3$) δ 169.7, 165.1, 149.4, 132.0, 117.6, 113.5, 52.6, 40.3; IR (neat) 1728, 1647, 1592, 1451 cm$^{-1}$; MS (m/e) 247 (M), 245 (M), 188, 186, 166 (base peak); HRMS calcd for C$_8$H$_8$O$_3$BrN 244.9687, found 244.9661.

N-Propargylation (70%) and C-ethylation (95%) then gave the precursor 11 for the 4+1 annulation. For C-ethylation, see Danishefsky, S. and Etheredge, S. J., *J. Org. Chem.*, 39, 3430 (1974), the disclosure of which is incorporated herein by reference.

In general, the solution of bromopyridone 10 (12.3 g, 50 mmol) in anhydrous ethylene glycol dimethyl ether (DME, 150 mL) was cooled to 0° C. to −10° C. Sodium hydride (60% suspension in mineral oil, 2.2 g, 55 mmol) was added in several portions under argon. The mixture was warmed to room temperature and stirred until hydrogen ceased to evolve (about 20 min at room temperature). Anhydrous lithium bromide (4.8 g, 55 mmol) was added. After 20 minutes, propargyl bromide (80% in toluene, 11.9 g, 100 mmol) and DMF (3.7 g, 50 mmol) were added. The mixture was heated at 65° C. for 16 hours. After solvent removal, methylene chloride and water were added to the residue. The organic layer was separated. The aqueous layer was extracted with methylene chloride. The combined organic phase was washed with water and brine, and dried over sodium sulfate. After solvent removal with a rotary evaporator, a small amount of ether was added to the residue, and solids precipitated. The solids were filtered and rinsed with ether to give approximately 9.34 g of methyl 2-(6-bromo-N-propargyl-2(1H)-pyridon-4-yl) acetate. The filtrate was concentrated and applied to column chromatography (silica gel, hexane/ethyl acetate) to give additional 1.1 g of the product as off-white solids. Total yield was 69–73%. The product contained 3–8% of the 6-chloro analogue as detected by GC. $^1$H NMR (300 MHz, CDCl$_3$) δ 6.50 (1 H, d, J=1.6 Hz), 6.43 (1H, d, J=1.6 Hz), 5.02 (2H, d, J=2.4 Hz), 3.72 (3H, s), 3.40 (2H, s), 2.29 (1H, t, J=2.4 Hz); $^{13}$C NMR (75 MHz, CDCl$_3$) δ 169.6, 161.7, 146.7, 126.3, 118.9, 112.9, 76.9, 72.6, 52.5, 40.1, 38.2; IR (neat) 3287, 1734, 1655, 1597 cm$^{-1}$; MS (m/e) 285 (M), 283 (M, base peak), 226, 224, 204, 176, 116;HRMS calcd for C$_{11}$H$_{10}$O$_3$BrN 282.9844, found 282.9850.

Under argon, methyl 2-(6-bromo-N-propargyl-2(1H)-pyridon-4-yl) acetate (852 mg, 3 mmol) was dissolved in DME (15 mL). The solution was cooled to −60° C., and potassium tert-butoxide (353 mg, 3.15 mmol) was added.

After 5 min at −60° C., the mixture was warmed to −15° C., then cooled to −60° C. again. Ethyl iodide (1.87 g, 12 mmol) was added. After 5 minutes at −60° C., the reaction mixture was kept in an ice-bath, and stirred overnight (0° C. to room temperature). Solvent was removed with a rotary evaporator. Methylene chloride (30 mL) and water (30 mL) were added. The organic layer was separated. The aqueous layer was extracted with methylene chloride. The combined organic phase was washed with brine, and dried over sodium sulfate. After solvent removal, the residue was applied to column chromatography (silica gel, chloroform) to give 890 mg of precursor 11a (methyl 2-(6-bromo-N-propargyl-2(1H) pyridon-4-yl) butyrate) in 95% yield. The product contained 5–10% of the 6-chloro analogue as detected by GC. $^1$H NMR (300 MHz, CDCl$_3$) δ 6.52 (1H, d, J=1.7 Hz), 6.44 (1H, d, J=1.7 Hz), 5.01 (2H, d, J=2.4H),3.69 (3H, s), 3.22 (1H, t, J=7.6 Hz), 2.30 (1H, t, J=2.4 Hz), 2.00 (1H, m), 1.72 (1H, m), 0.90 (3H, t, J=7.4 Hz); $^{13}$C NMR (75 MHz, CDCl$_3$) δ 172.2, 161.7, 151.4, 126.3, 117.8, 111.3, 76.8, 72.5, 52.4 (2 C), 38.2, 25.3, 11.9; IR (neat) 3264, 1732, 1663, 1509 cm$^{-1}$; MS (m/e) 313 (M, base peak), 311, 284, 282, 254, 252, 232, 204, 144;HRMS calcd for C$_{13}$H$_{14}$O$_3$BrN 311.0157, found 311.0139.

Reaction of 11a with phenyl isocyanide as described above gave pure 12a in 45% isolated yield.

Compound 12a was first prepared by Danishefsky, and has been a key intermediate in many syntheses of camptothecin. See Volkmann, R. Danishefsky, S., Eggler, J. and Soloman, D. M., *J. Am. Chem. Soc.*, 93, 5576 (1971); Cai, J. C. and Hutchinson, C. R., *Chem. Heterocycl. Compd.*, 25, 753 (1983); Hutchinson, C. R., *Tetrahedron*, 37, 1047 (1981); Cai, J. C. and Hutchinson, C. R., *The Alkaloids: Chemistry and Pharmacology*, Brossi, A. Ed., Academic Press: New York, Vol. 21, p. 101 (1983); and Schultz, A. G., *Chem. Rev.* 73, 385 (1973), the disclosures of which are incorporated herein by reference. Conversion of 12a to (±)-camptothecin is accomplished in two steps: hydroxymethylation (35%) and oxidation (quantitative). See Cai, J. C. and Hutchinson, C. R., *Chem. Heterocycl. Compd.*, 25, 753 (1983); Hutchinson, C. R., *Tetrahedron*, 37, 1047 (1981); Cai, J. C. and Hutchinson, C. R., *The Alkaloids: Chemistry and Pharmacology*, Brossi, A.. Ed., Academic Press: New York, Vol. 21, p. 101 (1983); and Schultz, A. G., *Chem. Rev.* 73, 385 (1973), the disclosures of which are incorporated herein by reference.

This synthesis of the key Danishefsky tetracycle 12a under the present method requires only six steps starting from dimethyl acetonedicarboxylate, and the overall yield is currently approximately 13%.

Figure 3:
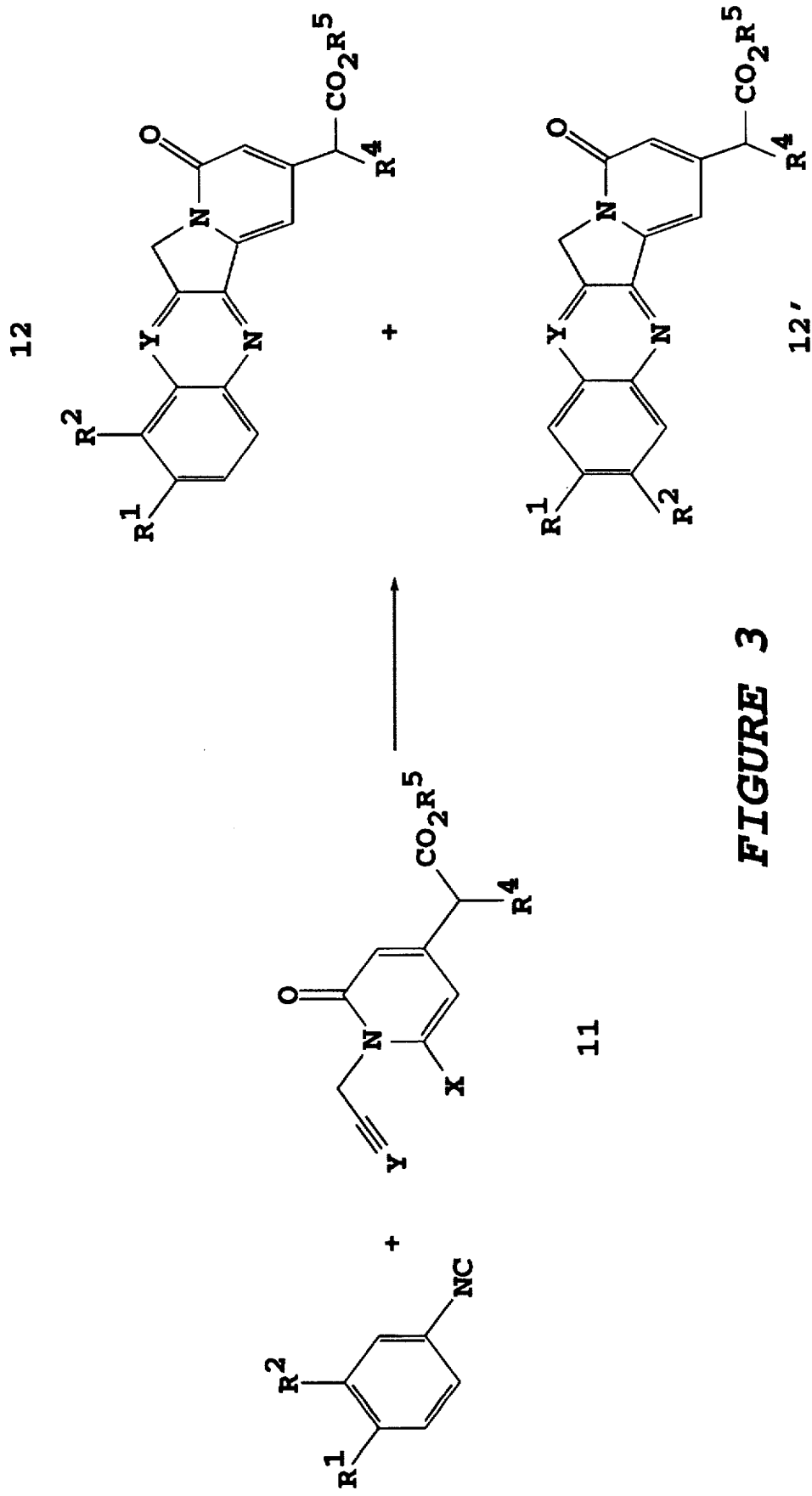
FIG. 3 is an illustration of the general synthetic scheme of the present 4+1 radical annulation.

A number of analogs of tetracycle 12a can be prepared under the present synthesis scheme. The general chemical equation for the 4+1 annulation of the present invention is given in FIG. 3. In FIG. 3, X of precursor 11 preferably comprises Cl, Br, or I. Y of precursor 11 may comprise N, or C—R$^3$. Regioisomers are possible when R$^2$ of tetracyclic intermediates 12 does not comprise hydrogen.

Several examples of preparation of tetracyclic intermediates via the present 4+1 annulation involving precursor 11 and an aryl isonitrile are provided below.

Preparation of Tetracyclic Intermediates

Example 1

Figure 4A:
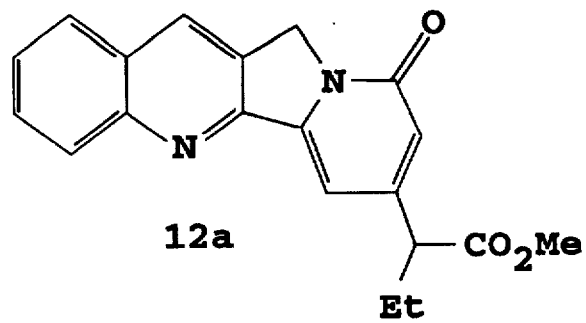
FIGS. 4a–4g provide illustrations of the chemical structures of several tetracyclic intermediates.

Under the general procedure, a benzene solution of precursor 11a (methyl 2-(6-bromo-N-propargyl-(1H)-pyridon-4-yl)butyrate), phenyl isocyanide (1.5 to 5 equiv) and hexamethylditin (0.7 to 1.5 equiv) in a flask (flat flask preferred) was irradiated under argon with a 275 W GE sunlamp or a 450 W Ace Hanovia lamp for 4 to 24 hours. Solvent and isocyanide were removed under reduced pressure. The residue was applied to column chromatography (silica gel, dichloromethane/methanol or hexanelacetone or chloroform/acetone) and/or MPLC (chloroform/ethyl acetate) to give corresponding tetracyclic intermediate 12a as illustrated in FIG. 4a.

Method A: A solution of precursor 11a (78 mg, 0.25 mmol), phenyl isocyanide (129 mg, 1.25 mmol), and hexamethylditin (123 mg, 0.375 mmol) in benzene (25 mL) in a flat flask was irradiated with a 275 W GE sunlamp at 80° C. for 20 hours. Solvent, isocyanide, and other volatile components were removed under reduced pressure. The residue was applied to MPLC (EM LiChroprep Si 60, chloroform/ethyl acetate=1.8/1) to give 37 mg of tetracycle 12a as illustrated in FIG. 4a. The yield was 45%.

Method B: A solution of precursor 11a (624 mg, 2 mmol), phenyl isocyanide (309 mg, 3 mmol), and hexamethylditin (982 mg, 3 mmol) in benzene (30 mL) in a flat flask was irradiated for 12 hours with a 450 W Ace Hanovia lamp. After removal of solvent, isocyanide, and other volatile components under reduced pressure, the residue was applied to column chromatography (silica gel, hexane/acetone 1.3:1, 1:1) to give 340 mg of crude product as brown solids. The crude product was ground with ether, filtered, and rinsed with ether to give 178 mg of tetracycle 12a as light yellow solids. The filtrate was concentrated and applied to MPLC to give additional 103 mg of tetracycle 12a, in 42% total yield.

Example 2

Figure 4B:
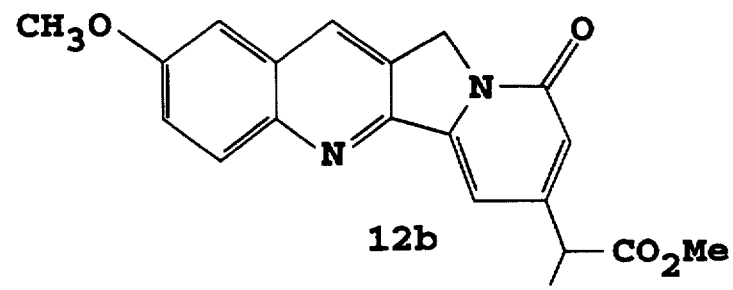

Following the procedure of Example 1, method A, except paramethoxyphenyl isocyanide (166 mg, 1.25 mmol) was substituted for phenyl isocyanide. MPLC (chloroform/ethyl acetate 1:1) afforded 30 mg of tetracycle 12b (as shown in FIG. 4b) as off-white solids in 33% yield. $^1$H NMR (300 MHz, CDCl$_3$) δ 8.16 (1H, s), 8.03 (1H, d, J=9.3 Hz), 7.40 (1 H, dd, J=9.3, 2.7 Hz), 7.21 (1H, d, J=1.0 Hz), 7.09 (1H, d, J=2.7 Hz), 6.58 (1H, d, J=1.0HZ), 5.15 (2H, s), 3.93 (3H, s), 3.69 (3H, s), 3.45 (1 H, t, J=7.6 Hz), 2.11 (1H, m), 1.90 (1H, m), 0.93 (3H, t, J=7.3 Hz); $^{13}$C NMR (75 MHz, CDCl$_3$) δ 172.7, 161.3, 158.7, 152.7, 150.4, 146.2, 144.9, 130.9, 129.4, 123.4, 129.3, 118.7, 105.4, 100.4, 96.1, 55.6, 53.2, 52.3, 49.7, 25.6, 12.0; IR (neat) 1730, 1667, 1601, 1240 cm$^{-1}$; MS (m/e) 364 (M, base peak), 336, 305, 278;HRMS calcd for C$_{12}$H$_{20}$O$_4$N$_2$ 364.1423, found 364.1477.

Example 3

Figure 4C:
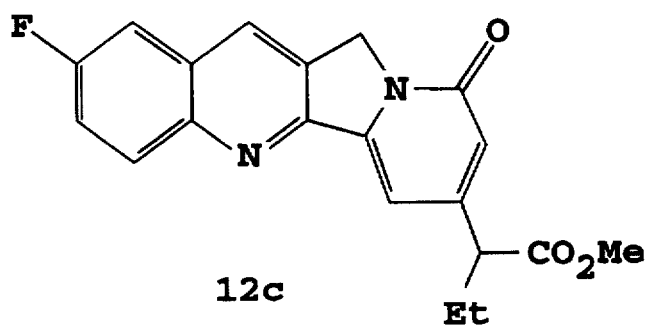

Following the procedure of Example 1, method A, except parafluorophenyl isocyanide (151 mg, 1.25 mmol) was substituted for phenyl isocyanide. MPLC (chloroform/ethyl acetate 2:1) afforded 29 mg of tetracycle 12c (shown in FIG. 4c) as light yellow solids in 33% yield. $^1$H NMR (300 MHz, CDCl$_3$) δ 8.30 (1H, s), 8.20 (1H, dd J=9.3, 5.4 Hz), 7.55 (2H, m), 7.29 (1H, d, J=1.3 Hz), 6.63 (1H, d, J=1.3 Hz), 5.24 (2H, s), 3.71 (3H, s), 3.48 (1H, t, J=7.7 Hz), 2.16 (1H, m), 1.90 (1H, m), 0.95 (3 H, t, J=7.3 Hz); $^{13}$C NMR (75 MHz, CDCl$_3$) δ 172.8, 161.3, 161.2 (J$_{CF}$=250.8 Hz), 152.7, 152.5, 146.0, 145.7, 132.2 (J$_{CF}$=8.3 Hz), 130.3, 129.7, 128.9 (J$_{CF}$= 10.2 Hz), 120.9 (J$_{CF}$=26.8 Hz), 119.6, 111.3 (J$_{CF}$=21.9 Hz), 100.9, 53.2, 52.4, 49.7, 25.7, 12.1; IR (neat) 1732, 1659, 1599 cm$^{-1}$; MS (m/e) 353 (M+1), 352 (M, base peak), 324, 293, 265;HRMS calcd for C$_{20}$H$_{17}$O$_3$FN$_2$ 352.1224, found 352.1248.

Example 4

Figure 4D:
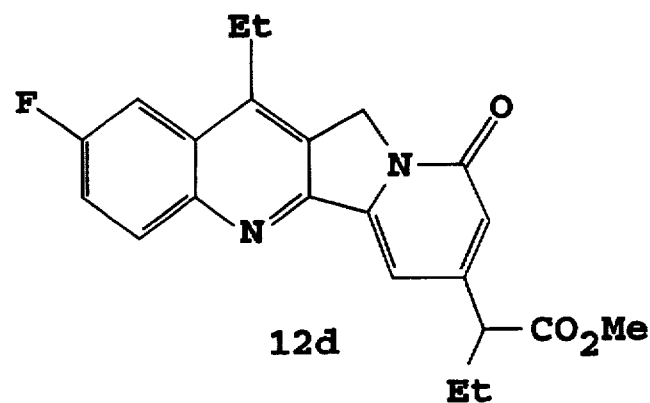

Following the procedure of Example 1, method B. A solution of methyl 2-(6-bromo-N-(2-pentyn-1 -yl)-2(1H)- pyridon-4-yl)butyrate (510 mg, 1.5 mmol) prepared from 10, parafluorophenyl isocyanide (272 mg, 2.25 mmol), and hexamethylditin (737 mg, 2.25 mmol) in benzene (22.5 mL) was irradiated for 17.5 h. Column chromatography (silica gel, hexane/acetone 1.5:1, 1:1) afforded 461 mg of crude product. The product was washed with ether to give 142 mg of tetracycle 12d (shown in FIG. 4d) as light yellow solids. The filtrate gave, after concentration and application to MPLC (chloroform/ethyl acetate 1.8:1), 54 mg of tetracycle 12d. Total yield was 33%. $^1$H NMR (300 MHz, CDCl$_3$) δ 8.18 (1H, dd, J =9.2, 5.6 Hz), 7.67 (1H, dd, J=9.9, 2.6 Hz), 7.54 (1H, td, J=9.2, 2.6 Hz), 7.28 (1H, s), 6.62 (1H, s), 5.19 (2H, s), 3.70 (3H, s), 3.47 (1H, t, J =7.7 Hz), 3.10 (2H, q, J=7.6 Hz), 2.14 (1H, m), 1.90 (1H, m), 1.36 (3H, t, J=7.6 Hz), 0.94 (3H, t, J=7.4 Hz); $^{13}$C NMR (75 MHz, CDCl$_3$) δ 172.7, 161.3, 161.2 ($J_{CF}$=250.2 Hz), 152.8, 151.9, 146.4, 146.3, 144.9, 133.0 ($J_{CF}$=9.4 Hz), 127.8 ($J_{CF}$=12.0 Hz), 127.7, 120.2 ($J_{CF}$=26.3 Hz), 119.3, 107.3 ($J_{CF}$=23.4 Hz), 100.9, 53.2, 52.3, 49.0, 25.6, 23.2, 13.8, 12.0; IR (neat) 1734, 1665, 1601 cm$^{-1}$; MS (m/e) 380 (M, base peak), 352, 321, 294; HRMS calcd for C$_{22}$H$_{21}$O$_3$FN$_2$ 380.1536, found 380.1539.

Examples 5.1–5.3

Figure 4E:
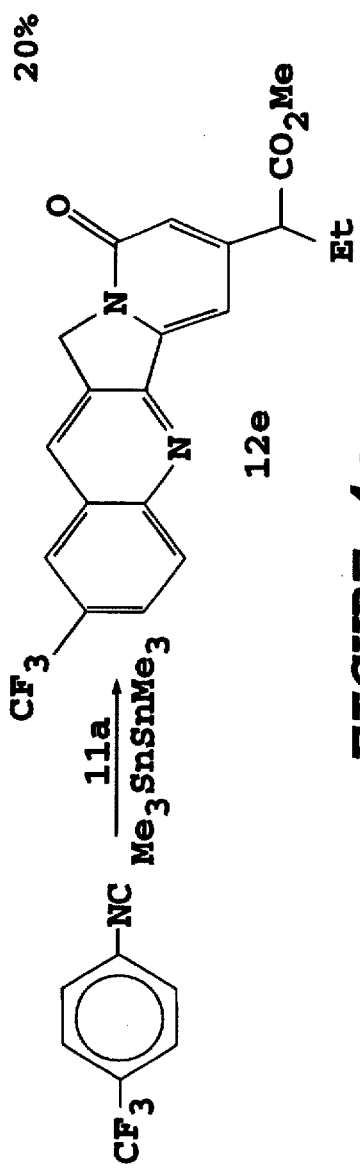
Figure 4F:
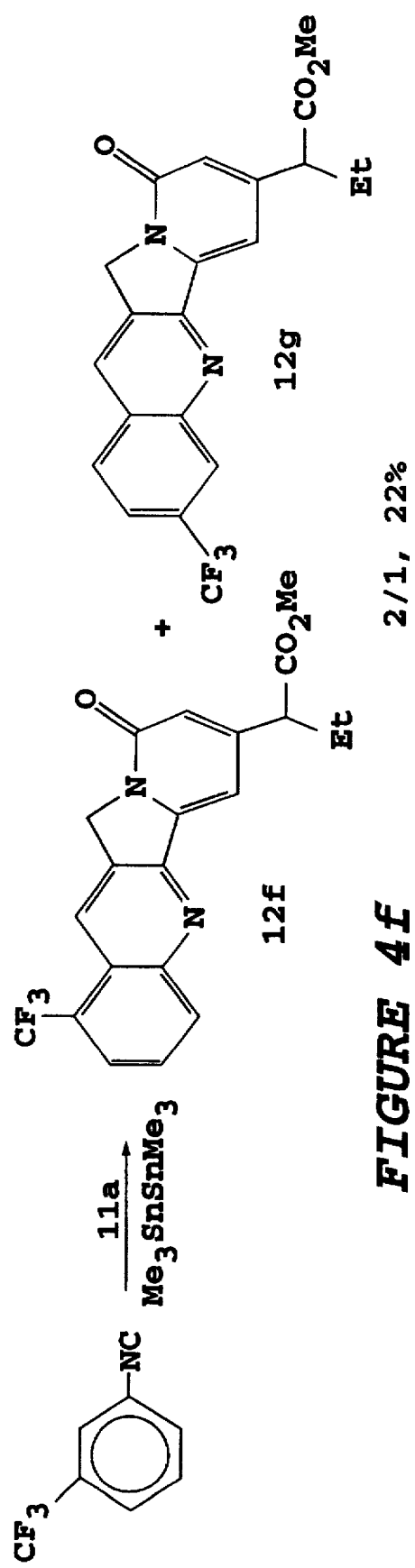
Figure 4G:
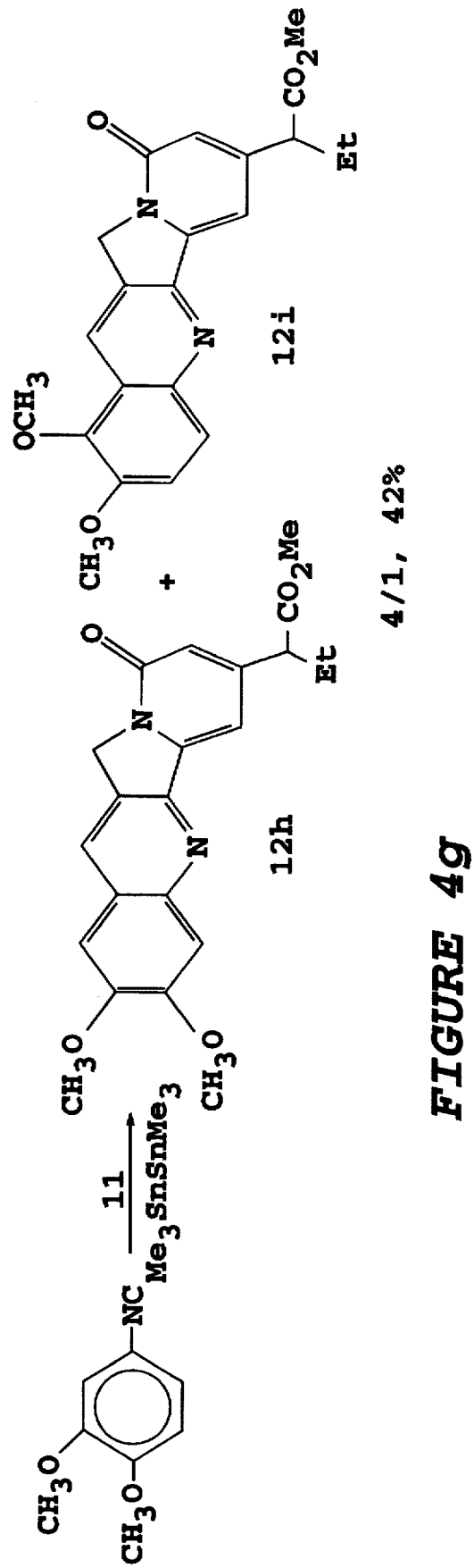

Further examples of tetracycle analogues obtained by substitution of various aryl isocyanides for phenyl isocyanide and otherwise following the procedure set forth in Example 1, method B, are set forth in FIG. 4e–4g. Tetracycle 12e (shown in FIG. 4e) was obtained in 20% yield. In the case of the meta-substituted isocyanide reactant shown in FIG. 4f, two isomeric tetracycles 12f and 12g were obtained in a 2:1 ratio. The combined yield was 22%. Similarly, in the case of the meta-substituted isocyanide reactant shown in FIG. 4g, two isomeric tetracycles 12h and 12i were obtained in a 4:1 ratio. The general formula of FIG. 3 illustrates such isomers as 12 and 12'. The combined yield in the case of tetracycle 12h and 12i was 42%.

Example 5.1

Example 1, method B was followed. A solution of 11a (156 mg, 0.5 mmol), para-trifluromethylphenylisocyanide (171 mg, 1 mmol), and hexamethylditin (246 mg, 0.75 mmol) in benzene (10 mL) was irradiated for 4 to 12 h. Column chromatography (silica gel, hexane/acetone 2:1, 1:1) followed by MPLC (chloroform/ethyl acetate 3.5:1) afforded 41 mg of 12e in 20% yield. $^1$H NMR (300 MHz, CDCl$_3$) δ 8.46 (1H, s), 8.33 (1H, d, J=8.9 Hz), 8.23 (1H, s), 7.97 (1H, dd, J=8.9, 1.6 Hz), 7.37 (1H, d, J=1.0 Hz), 6.68 (1H, d, J=1.0 Hz), 5.29 (2H, s), 3.72 (3H, s), 3.50 (1H, t, J=7.7 Hz), 2.18 (1H, m), 1.91 (1H, m), 0.97 (3H, t, J=7.4 Hz); $^{13}$C NMR (125 MHz, CDCl3) δ 172.7, 161.2, 155.1, 152.7, 149.8, 145.3, 131.9, 131.0, 131.1, 129.5, (q, $J_{CF}$=33 Hz), 127.0, 126.2 (2 ° C.), 123.8 (q, $J_{CF}$=271 Hz), 120.4, 101.8, 53.2, 52.5, 49.7, 25.7, 12.1; IR (neat) 1732, 1667, 1605, 1171, 1123 cm$^{-1}$; MS (m/e) 403, 402 (M, base peak), 383, 374, 343, 328, 315.

Example 5.2

Example 1, method B was followed. A solution of 11a (156 mg, 0.5 mmol), meta-trifluromethylphenylisocyanide (171 mg, 1 mmol), and hexamethylditin (246 mg, 0.75 mmol) in benzene (10 mL) was irradiated for 12 hours. Column chromatography (silica gel, hexane/acetone 2:1, 1:1) followed by MPLC (chloroform/ethyl acetate 11:1, 2.5:1) afforded 31 mg of 12f and 12g in 22% yield. 12f: $^1$H NMR (300 MHz, CDCl$_3$) δ 8.67 (1H, s), 8.39 (1H, d, J=8.5 Hz), 8.01 (1H, d, J=7.3 Hz), 7.84 (1H, t, J=7.9 Hz), 7.34 (1H, d, J=1.4 Hz), 6.67 (1H, d, J=1.4 Hz), 5.29 (2H, s), 3.72 (3H, s), 3.49 (1H, t, J=7.7 Hz), 2.17 (1H, m), 1.91 (1H, m), 0.96 (3H, t, J=7.4 Hz); $^{13}$C NMR (125 MHz, CDCl$_3$) δ 172.7, 161.2, 153.6, 152.7, 149.0, 145.2, 134.5, 130.3, 128.8, 127.6, 126.7 (q, $J_{CF}$=31 Hz), 126.3, 124.2, 124.0 (q, $J_{CF}$= 272 Hz), 120.2, 101.5, 53.2, 52.4, 50.0, 25.7, 12.1; IR (neat) 1736, 1671, 1609, 1306, 1167, 1121 cm$^{-1}$; MS (m/e) 403, 402 (M, base peak), 374, 343, 328, 315. 12 g: $^1$H NMR (300 MHz, CDCl$_3$) δ 8.53 (1H, s), 8.44 (1H, s), 8.06 (1H, d, J=8.6 Hz), 7.82 (1H, dd, J=8.6, 1.4 Hz), 7.35 (1H, d, J=1.4 Hz), 6.69 (1H, d, J=1.4 Hz), 5.30 (2H, s), 3.73 (3H, s), 3.50(1H, t, J=7.7 Hz), 2.18 (1H, m), 1.92 (1H, M), 0.97 (3H, t, J=7.4 Hz); $^{13}$C NMR (125 MHz, CDCl$_3$) δ 172.6, 161.2, 154.4, 152.8, 147.9, 145.2, 132.2 (q, $J_{CF}$=33 Hz), 131.0, 130.8, 129.4 (2 ° C.), 127.6, 123.8 (q, $J_{CF}$=271 Hz), 123.4, 120.2, 101.7, 53.2, 52.5, 49.8, 25.7, 12.1; IR (neat) 1736, 1665, 1592, 1325, 1188, 1165, 1129 cm$^{-1}$; MS (m/e) 403, 402 (M, base peak), 383, 374, 343, 328, 315;HRMS calcd for.

Example 5.3

Example 1, method B was followed. A solution of 11a (156 mg, 0.5 mmol), 3,4-dimetholxyphenylisocyanide (163 mg, 1 mmol), and hexamethylditin (246 mg, 0.75 mmol) in benzene (10 mL) was irradiated for 12 hours. Column chromatography (silica gel, hexane/acetone/methanol 1:1:0, 1:1:0.05) followed by MPLC (chloroform/ethyl acetate/ methanol 1:1:0, 1:1:0.1) afforded 18 mg of 12i and 66 mg of 12h in 42% total yield. 12i: $^1$H NMR (300 MHz, CDCl$_3$) δ 8.63 (1H, s), 7.98 (1 H, d, J=9.4 Hz), 7.60 (1H, d, J=9.4 Hz), 7.26 (1H, d, J=1.5 Hz), 6.62 (1H, d, J=1.5 Hz), 5.24 (2H, s), 4.05 (6H, s), 3.71 (3H, s), 3.47 (1H, t, J=7.8 Hz), 2.16 (1H, m), 1.90 (1H, m), 0.95 (3H, t, J=7.3 Hz); $^{13}$C NMR (125 MHz, CDCl$_3$) δ 8172.8, 161.4, 152.7, 151.2, 149.4, 146.1, 144.4, 142.1, 128.9, 125.8, 125.0, 124.1, 119.2, 118.7, 100.7, 61.5, 56.8, 53.2, 52.4, 50.0, 25.6, 12.1, IR (neat) 1732, 1662, 1595, 1267, 1169, 1096 cm$^{-1}$; MS (m/e) 395, 394 (M, base peak), 379, 366, 335, 308; 12h: $^1$H NMR (300 MHz, CDCl$_3$) δ 8.19 (1H, s), 7.51 (1H, s), 7.22 (1H, d, J=1.1 Hz), 7.13 (1H, s), 6.60 (1H, d, J=1.1 Hz), 5.20 (2H, s), 4.08 (3H, s), 4.06 (3H, s), 3.71 (3H, s), 6.60 (1H, d, J=1.1 Hz), 5.20 (2H, s), 4.08 (3H, s), 4.06 (3 H, s), 3.71 (3H, s), 3.47 (1H, t, J=7.7 Hz), 2.16 (1H, m), 1.90 (1H, m), 0.95 (3H, t, J=7.4 Hz); $^{13}$C NMR (125 MHz, CDCl$_3$) δ 172.7, 161.4, 153.3, 152.7, 150.9, 150.5, 146.5, 146.1, 128.9, 127.6, 124.3, 118.6, 107.9, 105.2, 100.1, 56.3, 56.2, 53.2, 52.3, 49.8, 25.5, 12.0; IR (neat) 1736, 1667, 1617, 1599, 1503, 1431, 1256, 1225 cm$^{-1}$; MS (m/e) 395, 394 (M, base peak), 366, 335, 320, 308.

Example 6.1–6.3

Figure 5:
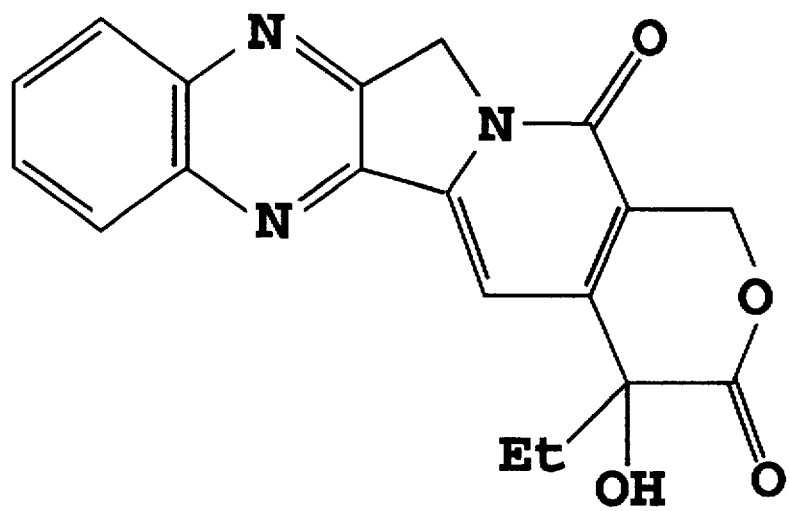
FIG. 5 is an illustration of a novel camptothecin analogue.

An interesting analogue of camptothecin potentially accessible by the present radical [4+1] annulation method is shown in FIG. 5. The quinoxaline ring system of this analogue would be formed by employing a nitrile (rather than an alkyne) as the radical acceptor Y in the pyridone precursor 11 of FIG. 3.

Several examples of synthesis of the requisite pyridinone precursors and the resulting tetracycle intermediates for the analogue of FIG. 5 and related compounds are given below.

Example 6.1

Figure 6:
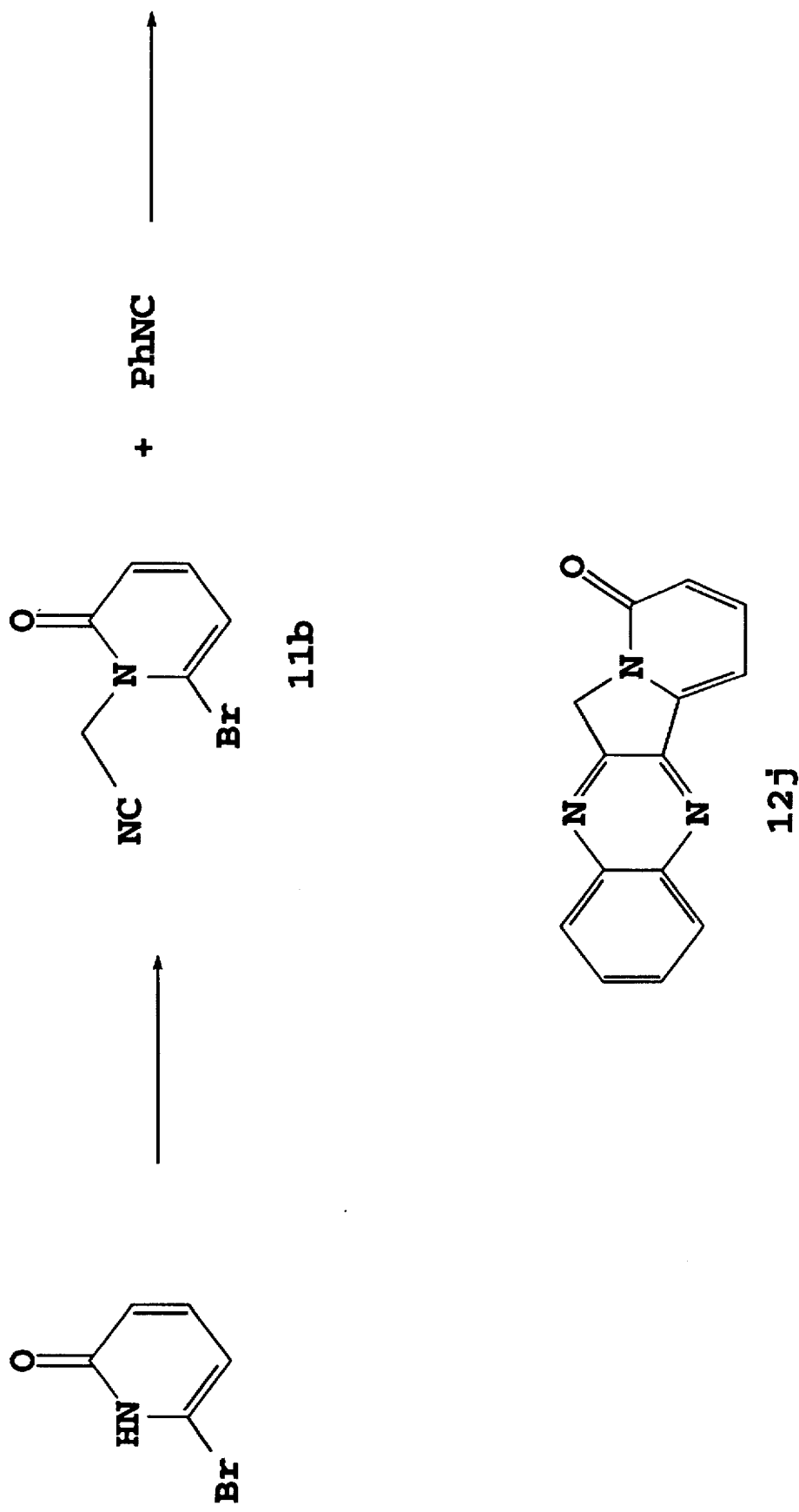
FIG. 6 provides an illustration of a model synthetic scheme for a novel tetracycle.

The precursor 11b of FIG. 6 was produced by first cooling a solution of 6-bromopyridone (1.0 g, 5.75 mmol) in DME (20 mL) to −60° C. Sodium hydride (252 mg of a 60% dispersion in oil, washed with hexanes and dried) was then added and the mixture was allowed to warm to room temperature. The mixture was stirred for 30 mins., until $H_2$ evolution had ceased. After this time, lithium bromide (550 mg, 6.32 mmol), bromoacetonitrile (1.38 g, 11.5 mmol) and DMF (665 μL) were added. The mixture was then heated at reflux for 16 hours. The indigo-colored reaction mixture was then concentrated at reduced pressure and the residue was partitioned between $CH_2Cl_2$ (20 mL) and water (20 mL). The aqueous phase was further extracted with $CH_2Cl_2$ (3×20 mL). The combined organic extracts were then dried, filtered and concentrated at reduced pressure. Flash chromatography (eluant, 1:1 hexane, ethyl acetate) of the crude product and concentration of the fractions containing material $R_f$=0.1 afforded the product pyridone precursor 11b as a colorless solid (730 mg, 64%). This material was recrystallized from $CHCl_3$/hexane to afford colorless needles, mp 100°–101° C. $^1$H NMR (300 MHz, $CDCl_3$) δ 7.23 (dd, J=9.3 and 7.0 Hz, 1H, H4), 6.58 (d, J=9.3 Hz, 1H), 6.56 (d, J=7.0 Hz, 1H), 5.18 (s, 2H). $^{13}$C NMR (75 MHz, $CDCl_3$) δ 161.66, 140.29, 125.32, 119.18, 113.80, 111.98, 35.99. IR (KBr) 2999, 2961, 1660, 1583, 1512, 800 cm$^{-1}$. MS m/e 212, 214 (M+), 184, 186 (M—CO), 133 (M—Br).

A solution of pyridone precursor 11b (100 mg, 0.469 mmol) in benzene (10 mL) containing hexamethylditin (222 mg, 0.678 mmol) and phenyl isocyanide (2.4 mL of a 1.0M solution in benzene) was heated at 80° C. and irradiated with an hanovia UV lamp for 16 hours. After this time the mixture was diluted with $Et_2O$ and shaken with 2M HCl and then filtered through a sintered glass funnel. The phases were then separated and the organic phase was extracted with 2M HCl (6×20 mL). The combined aqueous acidic phases were neutralized with NaOH and extracted with $CHCl_3$ (4×50 mL). The combined organic phases were then dried, filtered and concentrated at reduced pressure to afford a brown oil (110 mg). Preparative TLC of this material (1:1 acetone, $CH_2Cl_2$) and extraction of the yellow fluorescent band ($R_f$=0.5) gave the product tetracycle 12j as shown in FIG. 6 as a yellow solid (38 mg, 35%). $^1$H NMR (300MHz, $CDCl_3$) δ 8.20 (m, 2H), 7.88 (m, 2H), 7.68 (dd, J=8.7 and 7.0 Hz, 1H), 7.31 (d, J=6.7 Hz, 1H), 6.82 (d, J=8.9 Hz, 1H), 5.31 (s, 3H). $^{13}$C NMR (125 MHz, $CDCl_3$) δ 161.20, 152.95, 146.65, 144.22, 142.88, 142.74, 140.14, 131.31, 130.69, 129.87, 129.48, 122.25, 102.30, 50.55. IR (KBr) 3445, 2363, 2340, 1653 cm$^{-1}$. MS m/e 235 (M+), 207 (M—CO).

Example 6.2

Figure 7:
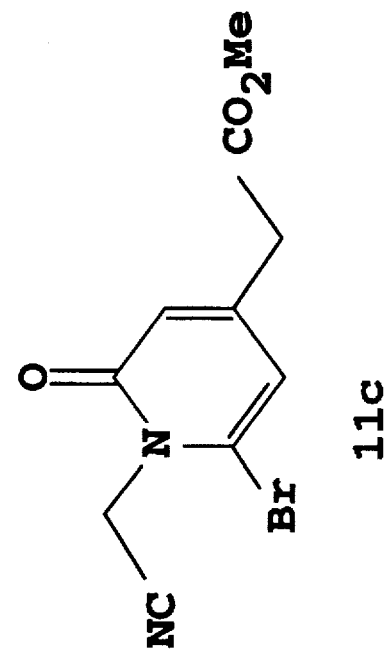
FIG. 7 provides a synthetic scheme for a novel precursor.
Figure 7:
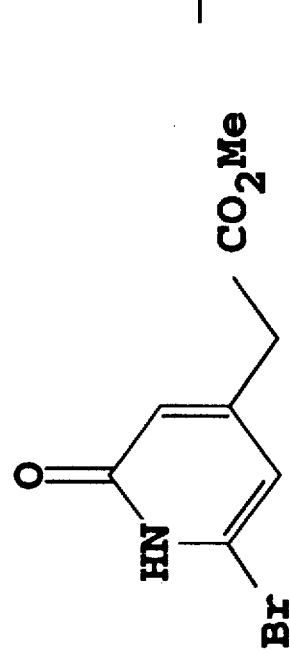

Precursor 11c of FIG. 7 was produced by first treating a solution of bromopyridone (1.5 g, 6.10 mmol) in DME (20 mL) at −60° C. with sodium hydride (267 mg of a 60% dispersion in oil). The mixture was allowed to warm to room temperature, and after evolution of hydrogen had ceased lithium bromide (585 mg, 6.72 mmol), bromoacetonitrile (1.46 g, 12.18 mmol) and DMF (720 μL) were added. The mixture was then heated at reflux for 16 hours. After usual workup and chromatographic purification, the product was afforded as a colorless solid (0.98 g, 56%, 64% based on recovered starting material). This material was recrystallized from $CHCl_3$/hexanes to give colorless prisms, mp 107°–109° C. $^1$H NMR (300 MHz, $CDCl_3$) δ 6.57 (s, 1H), 6.47 (s, 1H), 5.15 (s, 2H), 3.74 (s, 3H), 3.43 (s, 2H). $^{13}$C NMR (75 MHz, $CDCl_3$) δ 169.17, 161.17, 147.67, 125.05, 118.90, 113.71, 113.58, 52.58, 40.14, 35.75. IR (KBr) 3017, 2957, 2361, 2342, 1736, 1668, 1593, 1508cm$^{-1}$. MS m/e 284, 286 (M+), 245, 247 (M—$CH_2N$), 205 (M—Br, 100).

Example 6.3

A solution of pyridone precursor 11c (533 mg, 1.87 mmol) in DME (8 mL) was cooled to −70° C. KOtBu (0.23 g, 2.05 mmol) was added in one portion, and the solution immediately turned a bright yellow color. After 5 mins., ethyl iodide (0.62 g, 7.75 mmol) was added and the reaction mixture was stirred for 2 hours at −70° C. and then at room temperature for 20 hours. After this time the mixture was poured into water (20 mL) and extracted with $CH_2Cl_2$ (3×20 mL). The combined extracts were dried, filtered and then concentrated at reduced pressure. The residue obtained was purified by flash chromatography (eluant, 1:1 ethyl acetate, $CHCl_3$) to afford the product 11d of FIG. 8 as a colorless oil that solidified on standing (400 mg, 65%). This precursor 11d was recrystallized from CHCl3/hexanes to afford colorless prisms. $^1$H NMR (300 MHz, $CDCl_3$) δ 6.55 (s, 1H), 6.42 (s, 1H), 5.12 (s, 2H), 3.66 (s, 3H), 3.21 (t, J=7.6 Hz, 1H), 1.97 (m, 1H), 1.68 (m, 1H), 0.87 (t, J=7.3 Hz, 3H). $^{13}$C NMR (75 MHz, $CDCl_3$) δ 171.71, 161.11, 152.28, 125.07, 117.60, 113.72, 111.84, 52.26, 35.69, 32.52, 25.08, 11.68. IR (NaCl) 2967, 2359, 1736, 1671, 1597, 1200, 1169cm$^{-1}$. MS m/e314, 316 (M+), 233 (M—Br, 100).

Figure 8:
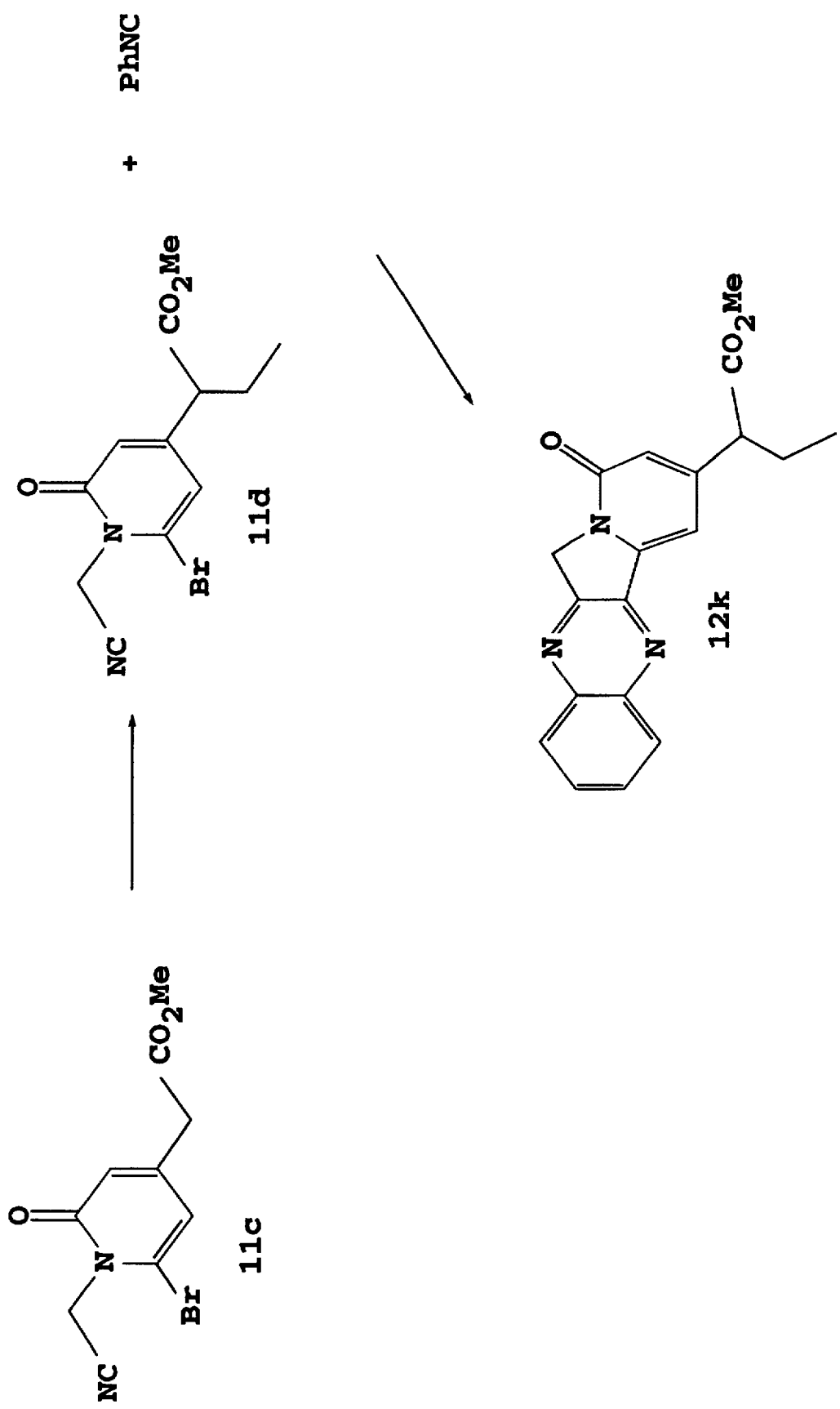
FIG. 8 provides an illustration of the synthetic scheme for a novel tetracycle intermediate.

According to FIG. 8, a solution of the bromopyridinone precursor 11d (120 mg, 0.383 mmol), phenyl isocyanide (2.0 mL of a 1.0M solution in benzene) and hexamethylditin (180 mg) in benzene (10 mL) was heated at 80° C. and irradiated with a Hanovia lamp for 20 hours. The mixture was then concentrated and the residue was purified by flash chromatography, (EtOAc/$CHCl_3$, 1:1). Fractions containing fluorescent material, $R_f$=0.3 were combined and concentrated to afford product tetracycle 12k as a yellow solid (14 mg, 11%). $^1$H NMR (300 MHz, $CDCl_3$) δ 8.20 (m, 2H), 7.88 (m, 2H), 7.35 (s, 1H), 6.71 (s, 1H), 5.28 (s, 2H), 3.73 (s, 3H), 3.49 (t, J=7.6 Hz, 1H), 2.16 (m, 1H), 1.90 (m, 1H), 0.97 (t, J=7.3 Hz, 3H). $^{13}$C NMR (125 MHz, $CDCl_3$) δ 172.65, 160.95, 153.10, 152.42, 146.51, 143.94, 142.84, 142.74, 131.38, 130.95, 129.89, 129.48, 121.05, 102.37, 53.19, 52.50, 50.37, 25.64 (one resonance not observed). IR (NaCl) 2973, 2386, 1738, 1659, 1651, 1622 cm$^{-1}$. MS m/e 335 (M+, 100), 307 (M—CO), 276 (M—$CO_2Me$).

Preparation of Aryl Isocyanides

Figure 9:
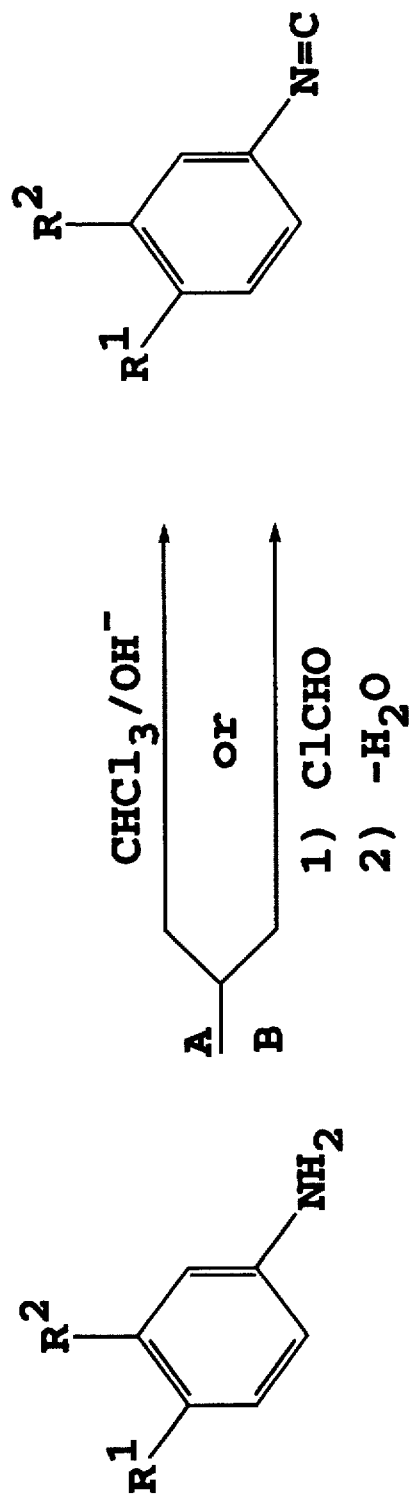
FIG. 9 provides an illustration of synthetic schemes for preparing aryl isocyanides.

The aryl isocyanides (e.g., phenyl isocyanide) for reaction with precursor 11 in the present synthesis are readily available from aryl amines by several standard methods as illustrated in FIG. 9. Typically, amines are reacted with base and chloroform (Method A of FIG. 9) or they are first converted to the respective formamides which are then dehydrated (Method B of FIG. 9). See Ugi, I., "Isonitrile Chemistry," Academic Press, NY, 10–17 (1971) and Walborsky, H., Org. Prep. Proced. Int., 11, 293–311 (1979), the disclosure of which are incorporated herein by reference.

Reaction of Aryl Isocyanides with Precursor 11

The reaction of precursor 11 with an aryl isocyanide to produce a tetracycle intermediate preferably takes place in the presence of a coreactant of the general formula given below:

$R_3M$—$MR_3$

In the above general formula, M comprises a metal or metalloid. Preferably M comprises Si, Ge or Sn. Most preferably M comprises Sn. R may comprise an alkyl or aryl group. Preferably the coreactant comprises hexamethylditin.

Several examples of the reaction of precursor 11a and phenyl isocyanide are given in Table 1 for hexabutylditin ($Bu_3Sn$)$_2$, hexamethyldisilane ($Me_3Si$)$_2$ and hexamethylditin ($Me_3Sn$)$_2$. The percent yields in Table 1 are for tetracycle intermediate 12a.

TABLE 1

| Coreactant | Phenyl isocyanide | Temp. | Time | Yield |
|---|---|---|---|---|
| [1] | | | | |
| 1.5 eq (Bu₃Sn)₂ | 5 eq | 80° C. | 24 hr. | 48% |
| 1.5 eq (Bu₃Sn)₂ | 1.5 eq | RT | 24 hr. | 35% |
| [2] | | | | |
| 1.5 eq (Me₃Si)₂ | 5 eq | 80° C. | 24 hr. | 45% |
| 1.5 eq (Me₃Si)₂ | 1.5 eq | RT | 24 hr. | 28% |
| [3] | | | | |
| 1.5 eq (Me₃Sn)₂ | 5 eq | 80° C. | 36 hr. | 58% |
| 1.5 eq (Me₃Sn)₂ | 1.5 eq | RT | 52 hr. | 56% |

Metal or metalloid hydrides may also be used as a coreactant.

While presently preferred embodiments of the present invention have been described in detail, the invention may be otherwise embodied within the scope of the appended claims.

What is claimed is:

1. A method of synthesizing the following intermediate in the synthesis of camptothecin:

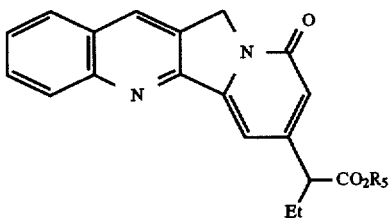

comprising the step of a 4+1 radical anuulation/cyclization wherein the precursor

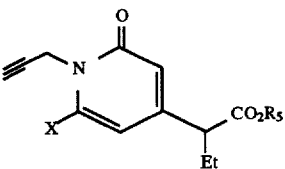

is reacted with phenyl isonitrile wherein X is selected from the group consisting of Br, Cl and I and wherein R5 is selected from the group consisting of an alkyl group and a benzyl group.

2. The method of claim 1 wherein the reaction of the precursor with a phenyl isonitrile takes place in the presence of a coreactant having the formula:

$$R_3M-MR_3$$

wherein M is selected from the group consisting of Si, Ge and Sn and wherein R is selected from the group consisting of an aryl group and an alkyl group.

3. The method of claim 2 wherein $R_3M-MR_3$ is hexamethylditin.

4. The method of claim 1 wherein X is Br.

5. The method of claim 2 wherein $R_3M-MR_3$ is hexabutylditin.

6. The method of claim 2 wherein $R_3M-MR_3$ is hexabutyldisilane.

* * * * *

UNITED STATES PATENT AND TRADEMARK OFFICE
CERTIFICATE OF CORRECTION

PATENT NO. : 5,744,605  
APPLICATION NO. : 08/609900  
DATED : April 28, 1998  
INVENTOR(S) : Dennis P. Curran, Hui Liu and Maree Patricia Collis It is certified that error appears in the above-identified patent and that said Letters Patent is hereby corrected as shown below:

Column 1, line 8, insert the following paragraph.

-- Governmental Interests  
This invention was made with government support under grant number RO1 GM33372 awarded by the National Institutes of Health. The government has certain rights in this invention. --

Signed and Sealed this

Fifteenth Day of January, 2008

JON W. DUDAS  
*Director of the United States Patent and Trademark Office*